United States Patent [19]

Schubert et al.

[11] Patent Number: 5,298,515
[45] Date of Patent: Mar. 29, 1994

[54] N-HETARYL-2-NITROANILINES

[75] Inventors: Juergen Schubert, Mannheim; Reiner Kober, Fussgoenheim; Gerhard Hamprecht, Weinheim; Hubert Sauter; Uwe Kardorff, both of Mannheim; Christoph Kuenast, Otterstadt, all of Fed. Rep. of Germany

[73] Assignee: BASF Aktiengesellschaft, Ludwigshafen, Fed. Rep. of Germany

[21] Appl. No.: 957,054

[22] Filed: Oct. 6, 1992

Related U.S. Application Data

[63] Continuation of Ser. No. 761,134, Sep. 17, 1991, abandoned.

[30] Foreign Application Priority Data

Sep. 20, 1990 [DE] Fed. Rep. of Germany ....... 4029771

[51] Int. Cl.$^5$ .................. C07D 277/42; A01N 43/78
[52] U.S. Cl. .................................. 514/361; 514/363; 514/370; 514/372; 514/447; 548/135; 548/138; 548/184; 548/193; 548/194; 548/213; 548/214; 549/61; 549/68
[58] Field of Search ............... 548/184, 193, 194, 213, 548/214, 135, 138; 549/61, 68; 514/361, 363, 370, 372, 447

[56] References Cited

U.S. PATENT DOCUMENTS

| | | | |
|---|---|---|---|
| 3,594,394 | 7/1971 | Chupp | 260/329 AM |
| 3,926,611 | 12/1975 | Tomlin et al. | 71/94 |
| 4,115,568 | 9/1978 | Chakrabarti et al. | |
| 4,659,363 | 4/1987 | Hubele et al. | 71/92 |

FOREIGN PATENT DOCUMENTS

| | | |
|---|---|---|
| 031257 | 7/1981 | European Pat. Off. |
| 0328954 | 8/1989 | European Pat. Off. |
| 1533236 | 11/1975 | United Kingdom |

OTHER PUBLICATIONS

Gupta, J. Ind. Chem Soc. 55 730 (1978).
Patent Abstracts of Japan, vol. 13, No. 472 (Oct. 25, 1989) citing Jpn 1-186849.
FR-A (Medicament) 7699 (1970).
Chem. Ber. 95 (1962) 2511.
Org. Mass Spectrom. 14 (1969) 1285.
Revue Roumaine de Chimie 14 (1969) 1285.
Zeitschrift für Naturforschung 30c (1975).

Primary Examiner—Robert Gerstl
Attorney, Agent, or Firm—Keil & Weinkauf

[57] ABSTRACT

Abstract of the Disclosure: N-Hetaryl-2-nitroanilines Ia and Ib

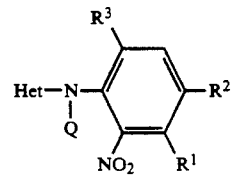

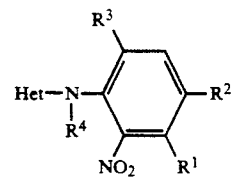

($R^1$=H, halogen, $C_1$-$C_4$-alkoxy; $R^2$=$NO_2$, CN, halogen, $C_1$-$C_4$-haloalkyl; $R^3$=$NO_2$, halogen, $C_1$-$C_6$-alkyl, $C_1$-$C_4$-haloalkyl; $R^4$=CO—$R^5$, CO—$OR^5$, $SO_2R^5$ with $R^5$=$C_1$-$C_4$-alkyl, substituted or unsubstituted phenyl or naphthyl; Q=H, alkali metal or alkaline earth metal ion, substituted or unsubstituted ammonium ion, phosphonium, sulfonium or sulfoxonium ion, one equivalent of a transition metal cation; Het=thienyl, thiazolyl, isothiazolyl or thiadiazolyl, each of which is linked via a ring carbon to the basic element, which can be fused to a non-aromatic $C_5$-$C_8$-ring and/or can additionally carry on each other carbon one of the following: CN, SCN, $NO_2$, halogen, alkyl, haloalkyl, cycloalkyl, alkoxy, alkylthio, substituted or unsubstituted phenyl, naphthyl, benzyl or thienyl, CO—$R^5$, CO—$OR^5$, $NR^6R^7$; $R^6$, $R^7$=$C_1$-$C_4$-alkyl, $C_2$-$C_4$-alkenyl, $C_2$-$C_4$alkynyl; excepting Ia where $R^1$=H, $R^2$ and/or $R^3$=$NO_2$ and Het=1,3,4-thiadiazol-2-yl substituted by $CF_3$ or $C(CH_3)_3$) can be used as pesticides.

4 Claims, No Drawings

N-HETARYL-2-NITROANILINES

This application is a continuation of application Ser. No. 07/761,134, filed on Sep. 17, 1991, now abandoned.

The present invention relates to novel N-hetaryl-2-nitroanilines of the formulae Ia and Ib

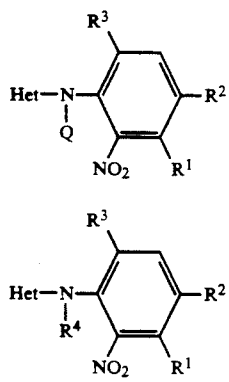

where
$R^1$ is hydrogen, halogen or $C_1$–$C_4$-alkoxy;
$R^2$ is nitro, cyano, halogen, partially or completely halogenated $C_1$–$C_4$-alkyl;
$R^3$ is nitro, halogen, $C_1$–$C_6$-alkyl, partially or completely halogenated $C_1$–$C_4$-alkyl;
$R^4$ is —CO—$R^5$, —CO—O$R^5$ or —SO$_2$$R_5$, with
$R^5$ being $C_1$–$C_4$-alkyl, phenyl or naphthyl, both of which can carry up to 3 halogen atoms and/or $C_1$–$C_4$-alkyl groups;
Q is hydrogen, an alkali metal or alkaline earth metal ion, an ammonium ion whose nitrogen can carry up to four $C_1$–$C_4$-alkyl, hydroxy-$C_1$–$C_4$-alkyl, phenyl and/or benzyl substituents, a phosphonium, sulfonium or sulfoxonium ion or an equivalent of a transition metal cation;
Het is thienyl, thiazolyl, isothiazolyl or thiadiazolyl, each of which is linked via a ring carbon to the basic element to which a non-aromatic $C_5$–$C_8$-ring can be fused and/or which can additionally carry on each other carbon one of the following substituents: cyano, thiocyanato, nitro, halogen, $C_1$–$C_4$-alkyl, partially or completely halogenated $C_1$–$C_4$-alkyl, $C_3$–$C_{10}$-cycloalkyl, $C_1$–$C_4$-alkoxy, $C_1$–$C_4$-alkylthio, phenyl, naphthyl, benzyl or thienyl, where each aromatic ring can carry up to three halogen atoms and/or $C_1$–$C_4$-alkyl groups; CO—$R^5$, CO—O$R^5$,N$R^6R^7$, where $R^6$ and $R^7$ are $C_1$–$C_4$-alkyl, $C_2$–$C_4$-alkenyl or $C_2$–$C_4$-alkynyl,
excepting those compounds Ia where $R^1$ is hydrogen, $R^2$ and/or $R^3$ is nitro and Het is 1,3,4-thiadiazol-2-yl which is substituted by trifluoromethyl or tert-butyl.

The present invention also relates to a process for preparing these compounds, to the use thereof and to the use of other compounds of type Ia as pesticides and to agents which contain all these compounds as active substances.

GB-A 1 533 236, DE-A 2 552 403, FR-A (Médicament) 7699, Chem. Ber. 95 (1962) 2511, Org. Mass Spectrom. 14 (1979) 171 and Revue Roumaine de Chimie 14 (1969) 1285 disclose N-hetaryl-2-nitroanilines which are of the type of compounds I but which differ from the novel compounds in the substitution pattern on the phenyl nucleus. They are used as intermediates or, in the case of the two French publications, as pharmaceutical active ingredients.

Furthermore, Zeitschrift für Naturforschung 30c (1975) 183 discloses N-(1,3,4-thiadiazol-2-yl)-2-nitroanilines which can carry in position 2, 4 or 6 of the aniline element two nitro groups and another substituent or three nitro groups. In the vegetable kingdom they act as decouplers and as inhibitors of photosynthetic electron transport.

No insecticidal action is mentioned in the specified publications.

EP-A 31257 describes N-pyridylanilines which have insecticidal activity and a substitution pattern on the aniline element which resembles that in compounds I. However, the action of these known pesticides on the pests and the duration of their action are not entirely satisfactory.

It is an object of the present invention to find novel substances which have insecticidal activity and which control the pests better than hitherto. We have found that this object is achieved by the N-hetaryl-2-nitroanilines of the formulae Ia and Ib defined above.

The substituents in the novel compounds Ia and Ib have the following specific meanings:

$R^1$
hydrogen;
halogen such as fluorine, chlorine, bromine and iodine, especially fluorine and chlorine;
unbranched or branched $C_1$–$C_4$-alkoxy such as methoxy, ethoxy, isopropoxy and tert-butoxy, preferably methoxy and ethoxy;

$R^2$
nitro or cyano;
halogen such as fluorine, chlorine, bromine and iodine, especially chlorine;
partially or completely halogenated $C_1$–$C_4$-alkyl, especially $C_1$–$C_2$-alkyl such as chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl and pentafluoroethyl, preferably trifluoromethyl;

$R^3$
nitro;
halogen such as fluorine, chlorine, bromine and iodine, especially chlorine;
unbranched or branched $C_1$–$C_4$-alkyl such as methyl, ethyl, propyl, 1-methylethyl, 1,1-dimethylethyl, 1-methylpropyl, 2-methylpropyl, n-butyl or tert-butyl;

$R^4$
—CO—$R^5$, —CO—O$R^5$ or —SO$_2$—$R^5$ with
$R^5$
unbranched or branched $C_1$–$C_4$-alkyl such as methyl, ethyl, propyl, 1-methylethyl, 1,1-dimethylethyl, 1-methylpropyl, 2-methylpropyl, n-butyl or tert-butyl;
phenyl or naphthyl, both of which can carry 1 to 3 halogen atoms, preferably fluorine and chlorine, and/or $C_1$–$C_4$-alkyl groups, preferably methyl and ethyl, especially phenyl, 4-fluorophenyl, 4-chlorophenyl, 4-bromophenyl, 2,4-dichlorophenyl,2-methylphenyl,3-methylphenyl, 4-methylphenyl, 2-nitrophenyl, 4-nitrophenyl, 1-naphthyl, 2-naphthyl and 4-chloro-1-naphthyl;

Particularly preferred are $C_1$-$C_4$-alkylcarbonyl such as methylcarbonyl, ethylcarbonyl, propylcarbonyl and tert-butylcarbonyl, $C_1$-$C_4$-alkoxycarbonyl such as methoxycarbonyl, ethoxycarbonyl, propoxycarbonyl, 1-methylethoxycarbonyl, butoxycarbonyl, 1-methylpropoxycarbonyl, 2-methylpropoxycarbonyl and 1,1-dimethylethoxycarbonyl and $C_1$-$C_4$-alkylsulfonyl such as methylsulfonyl, ethylsulfonyl, propylsulfonyl, 1-methylethylsulfonyl, butylsulfonyl, 1-methylpropylsulfonyl, 2-methylpropylsulfonyl and 1,1-dimethylethylsulfonyl.

Q
hydrogen;
an alkali metal or alkaline earth metal ion such as sodium, potassium, calcium, magnesium, barium;
an ammonium ion whose nitrogen can carry up to four $C_1$-$C_4$-alkyl, hydroxy-$C_1$-$C_4$-alkyl, phenyl and/or benzyl substituents, especially a diisopropylammonium, tetramethylammonium, tetrabutylammonium or trimethylbenzylammonium and trimethyl(2-hydroxyethyl)ammonium ion;
a phosphonium ion;
a sulfonium ion, especially a trialkylsulfonium ion or a sulfoxonium ion;
an equivalent of a transition metal cation, especially manganese, iron, copper and zinc;

Het: thienyl, thiazolyl, isothiazolyl, 1,2,4-thiadiazolyl or 1,3,4-thiadiazolyl, each of which is linked via a ring carbon to the basic structure and which can additionally carry on each other carbon one of the following substituents:
cyano, thiocyanato, nitro;
halogen, especially fluorine, chlorine and bromine;
$C_1$-$C_4$-alkyl such as methyl, ethyl, propyl, 1-methylethyl, butyl, 1-methylpropyl, 2-methylpropyl and 1,1-dimethylethyl, especially methyl and ethyl;
partially or completely halogenated $C_1$-$C_4$-alkyl, preferably $C_1$-$C_2$-alkyl such as chloromethyl, dichloromethyl trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl and pentafluoroethyl, especially trifluoromethyl;
$C_3$-$C_{10}$cycloalkyl which can be up to tricyclic in the case of the large rings and which can in each case be mono- or disubstituted by methyl, especially cyclopropyl, cyclobutyl, cyclopentyl, cyclohexyl, adamantyl, 1-methylcyclopropyl, 2-methylcyclopropyl, 2,2-dimethylcyclopropyl, 1-methylcyclopentyl and 1-methylcyclohexyl;
$C_1$-$C_4$-alkoxy such as methoxy, ethoxy, propoxy, 1-methylethoxy, butoxy, 1-methylpropoxy, 2-methylpropoxy and 1,1-dimethylethoxy, especially methoxy and ethoxy;
$C_1$-$C_4$-alkylthio such as methylthio, ethylthio, propylthio, 1-methylethylthio, butylthio, 1-methylpropylthio, 2-methylpropylthio and 1,1-dimethylethylthio, especially methylthio and ethylthio;
phenyl, naphthyl, benzyl or thienyl, where each aromatic ring can carry up to three halogen atoms, preferably fluorine and chlorine, and/or $C_1$-$C_4$-alkyl groups, preferably methyl and ethyl, especially phenyl, 1-naphthyl, 4-chloro-1-naphthyl, 2-thienyl and 5-chloro-2-thienyl;

CO—$R^5$, CO—O$R^5$, N$R^6R^7$, where $R^6$ and $R^7$ are $C_1$-$C_4$-alkyl, especially methyl and ethyl, $C_2$-$C_4$-alkenyl, especially ethenyl, allyl and 2-butenyl, or $C_2$-$C_4$-alkynyl, especially ethynyl and 2-propynyl; or the substituents on two adjacent carbon atoms form a $C_3$-$C_6$-methylene chain.

Particularly suitable heterocycles are 2-thienyl, 3-thienyl, 5-chloro-2-thienyl, 5-bromo-2-thienyl, 5-nitro-2-thienyl, 5-cyano-2-thienyl, 3-cyano-2-thienyl, 4-chloro-3-cyano-2-thienyl, 4-bromo-3-cyano-2-thienyl, 4-methyl-3-cyano-2-thienyl, 4-methyl-3,5-dicyano-2-thienyl, 4-methyl-3,5-bis(ethoxycarbonyl)-2-thienyl, 4-methyl-3,5-bis(methoxycarbonyl)-2-thienyl, 4-methyl-3-cyano-5-methoxycarbonyl-2-thienyl, 4-methyl-5-cyano-3-methoxycarbonyl-2-thienyl, 4,5-tetramethylene-3-ethoxycarbonyl-2-thienyl, 4,5-tetramethylene-3-methoxycarbonyl-2-thienyl, 4,5-trimethylene-3-methoxycarbonyl-2-thienyl, 4,5-tetramethylene-3-cyano-2-thienyl, 4-methoxycarbonyl-3-thienyl, 4-ethoxycarbonyl-3-thienyl, 4-cyano-3-thienyl, 4-nitro-3-thienyl, 4,5-dichloro-3-thienyl, 2-cyano-3-thienyl, 2-methoxycarbonyl-3-thienyl, 2-methoxycarbonyl-4-nitro-3-thienyl, 2-ethoxycarbonyl-4-nitro-3-thienyl, 2-ethoxycarbonyl-4-cyano-3-thienyl, 2-methoxycarbonyl-4-cyano-3-thienyl, 2-methoxycarbonyl-4-cyano-5-methyl-3-thienyl, 2-methoxycarbonyl-4-nitro-5-methyl-3-thienyl, 2,4-dicyano-3-thienyl, 2,4-dicyano-5-methyl-3-thienyl, 2-cyano-4-nitro-3-thienyl, 2-cyano-4-nitro-5-methyl-3-thienyl, 5-isothiazolyl, 3-methyl-5-isothiazolyl, 3-methyl-4-thiocyanato-5-isothiazolyl, 3-methyl-4-bromo-5-isothiazolyl, 3-methyl-4-chloro-5-isothiazolyl, 3-methyl-4-cyano-5-isothiazolyl, 3-methyl-4-nitro-5-isothiazolyl, 3-methyl-4-methoxycarbonyl-5-isothiazolyl, 3-phenyl-4-cyano-5-isothiazolyl, 3-phenyl-4-nitro-5-isothiazolyl, 3-phenyl-4-bromo-5-isothiazolyl, 3-phenyl-4-chloro-5-isothiazolyl, 3-phenyl-4-methoxycarbonyl-5-isothiazolyl, 3-benzyl-4-cyano-5-isothiazolyl, 3-benzyl-4-nitro-5-isothiazolyl, 3-benzyl-4-bromo-5-isothiazolyl, 3-benzyl-4-chloro-5-isothiazolyl, 3-benzyl-4-methoxycarbonyl-5-isothiazolyl, 2-thiazolyl, 5-chloro-2-thiazolyl, 5-bromo-2-thiazolyl, 5-methyl-2-thiazolyl, 5-methoxy-2-thiazolyl, 5-methylthio-2-thiazolyl, 5-ethoxy-2-thiazolyl, 5-ethylthio-2-thiazolyl, 5-cyano-2-thiazolyl, 5-methoxycarbonyl-2-thiazolyl, 5-ethoxycarbonyl-2-thiazolyl, 5-trifluoromethyl-2-thiazolyl, 5-(4-chlorophenyl)-2-thiazolyl, 5-(2,4-dichlorophenyl)-2-thiazolyl, 5-benzyl-2-thiazolyl, 4-cyano-2-thiazolyl, 4-methoxycarbonyl-2-thiazolyl, 4-ethoxycarbonyl-2-thiazolyl, 4-methyl-2-thiazolyl, 4-cyclohexyl-2-thiazolyl, 4-adamantyl-2-thiazolyl, 4-chloro-2-thiazolyl, 4-bromo-2-thiazolyl, 4-nitro-2-thiazolyl, 4-trifluoromethyl-2-thiazolyl, 4-(2,4-dichlorophenyl)-2-thiazolyl, 4-(4-fluorophenyl)-2-thiazolyl, 4-(4-chlorophenyl)-2-thiazolyl, 4-(1-naphthyl)-2-thiazolyl, 4-(4-chloro-1-naphthyl)-2-thiazolyl, 4-(2-thienyl)-2-thiazolyl, 4-(5-chloro-2-thienyl)-2-thiazolyl, 4-chloro-5-trifluoromethyl-2-thiazolyl, 4-chloro-5-nitro-2-thiazolyl, 4-chloro-5-cyano-2-thiazolyl, 4-bromo-5-cyano-2-thiazolyl, 4-bromo-5-trifluoromethyl-2-thiazolyl, 4-cyano-5-diallylamino-2-thiazolyl, 4-nitro-5-diallylamino-2-thiazolyl, 1,3,4-thiadiazol-2-yl, 5-chloro-1,3,4-thiadiazol-2-yl, 5-bromo-1,3,4-thiadiazol-2-yl, 5-methyl-1,3,4-thiadiazol-2-yl, 5-nitro-1,3,4-thiadiazol-2-yl, 5-cyano-1,3,4-thiadiazol-2-yl, 5-methoxycarbonyl-1,3,4-thiadiazol-2-yl, 5-methoxy-1,3,4-thiadiazol-2-yl, 5-methylthio-1,3,4-thiadiazol-2-yl, 5-trifluoromethyl-1,3,4-thiadiazol-2-yl, 5-benzyl-1,3,4-thiadiazol-2-yl, 5-phenyl-1,3,4-thiadiazol-2-yl, 5-(4-chlorophenyl)-1,3,4-thiadiazol-2-yl, 5-(4-fluorophenyl)-1,3,4-thiadiazol-2-yl, 5-(2,4-dichlorophenyl)-1,3,4-thiadiazol-2-yl, 1,2,4-thiadiazol-5-yl, 3-methyl-1,2,4-thiadiazol-5-yl, 3-methylthio-1,2,4-thiadiazol-5-yl, 3-methoxy-1,2,4-thiadiazol-5-yl, 3-cyano-1,2,4-thiadiazol-5-yl, 3-chloro-1,2,4-thiadiazol-5-yl, 3-bromo-1,2,4-thiadiazol-5-yl, 3-trifluoromethyl-1,2,4-thiadiazol-5-yl, 3-(4-chlorophenyl)-1,2,4-thiadiazol-5-yl.

The N-hetaryl-2-nitroanilines Ia are particularly preferred, and N-[3,5-diethoxycarbonyl-4-methyl-2-thienyl]-2,4-dinitro-6-trifluoromethylaniline, N-[4-bromo-3-methyl-5-isothiazolyl]-2,6-dinitro-4-trifluoromethylaniline, N-(5-chloro-2-thiazolyl)-2,6-dinitro-3-chloro-4-trifluoromethylaniline and N-(5-bromo-2-thiazolyl)-2,6-dinitro-3-chloro-4-trifluoromethylaniline are very particularly preferred.

N-hetaryl-2-nitroanilines Ia and Ib can be obtained in a variety of ways, specifically by the following preferred methods:

a) Reacting halogen-containing heteroaromatic compounds with 2-nitroanilines or reacting hetarylamines with 2-nitrohalobenzenes to give the compounds Ia where Q is hydrogen:

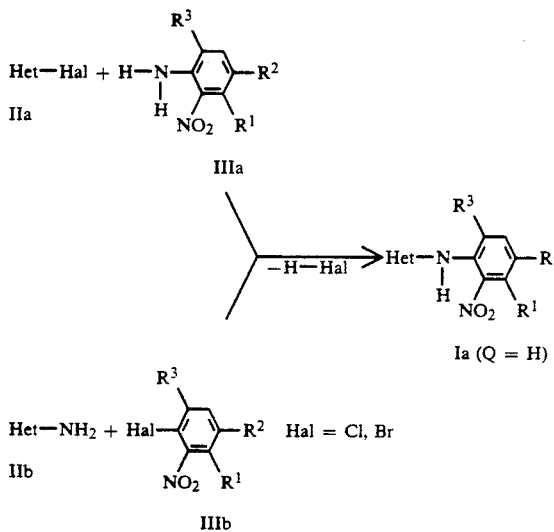

The reaction is normally carried out in an inert solvent or diluent, advantageously in the presence of a base.

Suitable solvents are aliphatic hydrocarbons such as cyclohexane and petroleum ether, aromatic hydrocarbons such as toluene, o-, m- and p-xylene, halohydrocarbons such as methylene chloride, chloroform and chlorobenzene, ethers, such as diethyl ether, diisopropyl ether tert-butyl methyl ether, dioxane, anisole and tetrahydrofuran, nitriles such as acetonitrile, propionitrile and dimethylformamide, ketones such as acetone, methyl ethyl ketone and diethyl ketone, alcohols such as methanol, ethanol, n-propanol, isopropanol, n-butanol and tert-butanol, and dimethyl sulfoxide; tetrahydrofuran, dioxane, dimethylformamide and tert-butanol are particularly preferred. It is also possible to use mixtures of the said solvents.

It is advisable in the case of oxidation-sensitive reactants to use an anhydrous solvent under an inert gas atmosphere, such as nitrogen, helium or argon, preferably nitrogen.

Suitable bases are, in general, inorganic compounds, for example alkali metal and alkaline earth metal hydroxides such as lithium hydroxide, sodium hydroxide, potassium hydroxide, calcium hydroxide, alkali metal and alkaline earth metal oxides such as lithium oxide, sodium oxide, calcium oxide and magnesium oxide, alkali metal hydrides such as lithium hydride and sodium hydride, alkaline earth metal hydrides such as calcium hydride, alkali metal amides such as lithium amide, sodium amide and potassium amide, alkali metal and alkaline earth metal carbonates such as sodium carbonate, potassium carbonate and calcium carbonate, and alkali metal bicarbonates such as sodium bicarbonate, organometallic compounds, especially alkali metal alkyls such as methyllithium and butyllithium, alkylmagnesium halides such as methylmagnesium chloride and alkali metal and alkaline earth metal alcoholates such as sodium methanolate, sodium ethanolate, potassium ethanolate, potassium tert-butanolate and dimethoxymagnesium, and organic bases, e.g. tertiary amines such as trimethylamine, triethylamine, diisopropylethylamine and N-methylpiperidine, pyridine, substituted pyridines such as collidine, lutidine and 4-dimethylaminopyridine, and bicyclic amines. Potassium hydroxide, sodium hydroxide, potassium carbonate, sodium ethanolate and potassium tert-butanolate, and triethylamine, are particularly preferred.

The starting compounds II and III are advantageously employed in approximately the stoichiometric ratio, but an excess of one of the components, for example up to about 10%, may be advantageous in some cases.

The amount of base is not critical, but for complete reaction, as a rule, at least the stoichiometric amount of base relative to II or III is required; it is preferable to use an excess of up to about 100 mol % of base.

The reaction is generally carried out at from −20° C. to the boiling point of the solvent, preferably at from 0° to 50° C.

Since the reaction does not depend on pressure, it is advantageously carried out under atmospheric pressure or the autogenous pressure of the solvent.

The starting compounds IIa and IIIa are known or can be prepared by conventional processes.

b) Reacting N-hetaryl-2-nitroanilines Ia with acylating or sulfonating agents IV

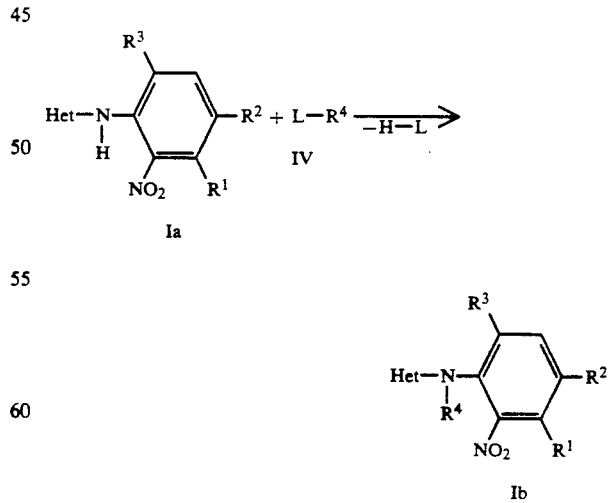

where L is a nucleophilic leaving group, especially a sulfonyl radical such as methylsulfonyl, trifluoromethylsulfonyl, p-toluenesulfonyl, p-bromophenylsulfonyl, or ethoxy or phenoxy, or a carboxylate radical such as acetate, particularly preferably halogen, such as chlorine, bromine and iodine.

The reaction is normally carried out in an inert solvent or diluent, especially in an aprotic solvent as mentioned for method a).

All the starting compounds are advantageously employed in approximately the stoichiometric ratio, but in some cases an excess of one of the components, for example up to about 10 mol %, may be advantageous.

Concerning the bases which can be used and the pressure, the statements made for method a) apply.

The reaction is generally carried out at from $-20°$ C. to the boiling point of the solvent, in particular at from 20° to 150° C.

The acylating and sulfonating agents IV are known or can be prepared by conventional processes.

The compounds Ia and Ib can be purified by conventional methods, e.g. by recrystallization, extraction and chromatography.

The proton on the nitrogen of the aniline element in the N-hetaryl-2-nitroanilines Ia can easily be eliminated. Hence the compounds Ia have acidic properties and they easily form basic salts with bases.

The N-hetaryl-2-nitroanilines can be used as pesticides.

The N-hetaryl-2-nitroanilines Ia' and Ib are suitable for effectively controlling pests from the classes of insects, arachnids and nematodes. They can be employed as pesticides in crop protection and in the hygiene, store protection and veterinary sectors.

The insect pests include:

from the order of Lepidoptera, for example *Agrotis ypsilon, Agrotis segetum, Alabama argillacea, Anticarsia gemmatalis, Argyresthia conjugella, Autographs gamma, Bupalus piniarius, Cacoecia murinana, Capua reticulana, Cheimatobia brumata, Choristoneura fumiferana, Choristoneura occidentalis, Cirphis unipuncta, Cydia pomonella, Dendrolimus pini, Diaphania nitidalis, Diatraea grandiosella, Earias insulana, Elasmopalpus lignosellus, Eupoecilia ambiguella, Evetria bouliana, Feltia subterranea, Galleria mellonella, Grapholita funebrana, Grapholita molests, Heliothis armigera, Heliothis virescens, Heliothis zea, Hellula undalis, Hibernia defoliaria, Hyphantria cunea, Hyponomeuta malinellus, Keifferia lycopersicella, Lambdina fiscellaria, Laphygma exigua, Leucoptera coffeella, Leucoptera scitella, Lithocolletis blancardella, Lobesia botrana, Loxostege sticticalis, Lymantria dispar, Lymantria monacha, Lyonetia clerkella, Malacosoma neustria, Mamestra brassicae, Orgyia pseudotsugata, Ostrinia nubilalis, Panolis flamea, Pectinophora gossypiella, Peridroma saucia, Phalera bucephala, Phthorimaea operculella, Phyllocnistis citrella, Pieris brassicae, Plathypena scarbra, Plutella xylostella, Pseudoplusia includens, Phyacionia frustrana, Scrobipalpula absolute, Sitotroga cerelella, Sparganothis pilleriana, Spodoptera frugiperda, Spodoptera littoralis, Spodoptera litura, Thaumatopoea pityocampa, Tortrix viridana, Trichoplusia ni* and *Zeiraphera canadensis;* from the order of Coleoptera, for example *Agrilus sinuatus, Agriotes lineatus, Agriotes obscurus, Amphimallus solstitialis, Anisandrus dispar, Anthonomus grandis, Anthonomus pomorum, Atomaria linearis, Blastophagus piniperda, Blitophaga undata, Bruchus rufimanus, Bruchus pisorum, Bruchus lentis, Byctiscus betulae, Cassida nebulosa, Cerotoma trifurcata, Ceuthorrhynchus assimilis, Ceuthorrhynchus napi, Chaetocnema tibialis, Conoderus vespertinus, Crioceris asparagi, Diabrotica longicornis, Diabrotica 12-punctata, Diabrotica virgifera, Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius californicus, Lissorhoptrus oryzophilus, Melanotus communis, Meligethes aeneus, Melolontha hippocastani, Melolontha melolontha, Onlema oryzae, Otiorrhynchus sulcatus, Otiorrhynchus ovatus, Phaedon cochleariae, Phyllotreta chrysocephala, Phyllophaga sp., Phyllopertha horticola, Phyllotreta nemorum, Phyllotreta striolata, Popillia japonica, Sitona lineatus* and *Sitophilus granaria;* from the order of Diptera, for example *Aedes aegypti, Aedes vexans, Anastrepha ludens, Anopheles maculipennis, Ceratitis capitata,, Chrysomya bezziana, Chrysomya hominivorax, Chrysomya macellaria, Contarinia sorghicola, Cordylobia anthropophaga, Culex pipiens, Dacus cucurbitae, Dacus oleae, Dasineura brassicae, Fannia canicularis, Gasterophilus intestinalis, Glossia morsitans, Haematobia irritans, Haplodiplosis equestris, Hylemyia platura, Hypoderma lineata, Liriomyza sativae, Liriomyza trifolii, Lucilia caprina, Lucilia cuprina, Lucilia sericata, Lycoria pectoralis, Mayetiola destructor, Musca domestics, Muscina stabulans, Oestrus ovis, Oscinella frit, Pegomya hyoscyami, Phorbia antiqua, Phorbia brassicae, Phorbia coarctata, Rhagoletis cerasi, Rhagoletis pomonella, Tabanus bovinus, Tipula oleracea* and *Tipula paludosa;* from the order of Thysanoptera, for example *Frankliniella fusca, Frankliniella occidentalis, Frankliniella tritici, Scirtothrips citri, Thrips oryzae, Thrips palmi* and *Thrips tabaci;* from the order of Hymenoptera, for example *Athalia rosae, Atta cephalotes, Atta sexdens, Atta texana, Hoplocampa minuta, Hoplocampa testudinea, Monomorium pharaonis, Solenopsis geminata* and *Solenopsis invicta;* from the order of Heteroptera, for example *Acrosternum hilare, Blissus leucopterus, Cyrtopeltis notatus, Dysdercus cingulatus, Dysdercus intermedius, Eurygaster integriceps, Euchistus impictiventris, Leptoglossus phyllopus, Lygus lineolaris, Lygus pratensis, Nezara viridula, Piesma quadrata, Solubea insularis* and *Thyanta perditor;* from the order of Homoptera, for example *Acyrthosiphon onobrychis, Adelges laricis, Aphidula nasturtii, Aphis fabae, Aphis pomi, Aphis sambuci, Brachycaudus cardui, Brevicoryne brassicae, Cerosipha gossypii, Dreyfusia nordmannianae, Dreyfusia piceae, Dyasphis radicola, Dysaulacorthum pseudosolani, Empoasca fabae, Macrosiphum avenae, Macrosiphum euphorbias, Macrosiphon rosae, Megoura viciae, Metopolophium dirhodum, Myzodes persicae, Myzus cerasi, Nilaparvata lugens, Pemphigus bursarius, Perkinsiella saccharicida, Phorodon humuli, Psylla mali, Psylla piri, Rhopalomyzus ascalonicus, Rhopalosiphum maidis, Sappaphis mala, Sappaphis mali, Schizaphis graminum, Schizoneura lanuginosa, Trialeurodes vaporariorum* and *Viteus vitifolii;* from the order of Isoptera, for example *Calotermes flavicollis, Leucotermes flavipes, Reticulitermes lucifugus* and *Termes natalensis;* from the order of Orthoptera, for example *Acheta domestica, Blatta orientalis, Blattella germanica, Forficula auricularia, Gryllotalpa gryllotalpa, Locusta migratoria, Melanoplus birittatus, Melanoplus femurrubrum, Melanoplus mexicanus, Melanoplus sanguinipes, Melanoplus spretus, Nomadacris septemfasciata, Periplaneta americana, Schistocerca americana, Schistocerca peregrina, Stauronotus maroccanus* and *Tachycines asynamorus;* from the class of Arachnoidea, for example arachnids (Acarina) such as *Amblyomma americanum, Amblyomma variegatum, Argas persicus, Boophilus annulatus,*

*Boophilus decoloratus, Boophilus microplus, Brevipalpus phoenicis, Bryobia praetiosa, Dermacentor silvarum, Eotetranychus carpini, Eriophyes sheldoni, Hyalonnna truncatum, Ixodes ricinus, Ixodes rubicundus, Ornithodorus moubata, Otobins megnini, Paratetranychus pilosus, Permanyssus gallinae, Phyllocaptrata oleivora, Polyphagotarsonemus latus, Psoroptes ovis, Rhipicephalus appendiculatus, Rhipicephalus evertsi, Saccoptes scabiei, Tetranychus cinnabarinus, Tetranychus kanzawai, Tetranychus pacificus, Tetranychus telarius* and *Tetranychus urticae;* from the class of nematodes, for example root knot nematodes, e.g. *Meloidogyne hapla, Meloidogyne incognita, Meloidogyne javanica*, cyst-forming nematodes, e.g. *Globodera rostochiensis, Heterodera avenae, Heterodera glycinae, Heterodera schatii, Heterodera trifolii*, stem and leaf eelworms, e.g. *Belonolaimus longicaudatus, Ditylenchus destructor, Ditylenchus dipsaci, Heliocotylenchus multicinctus, Longidorus elongatus, Radopholus similis, Rotylenchus robustus, Trichodorus primitivus, Tylenchorhynchus claytoni, Tylenchorhynchus dubius, Pratylenchus neglectus, Pratylenchus penetrans, Pratylenchus curvitatus* and *Pratylenchus goodeyi.*

The active ingredients can be applied as such or as formulations thereof or application forms prepared therefrom, e.g. in the form of directly sprayable solutions, powders, suspensions or dispersions, emulsions, oil dispersions, pastes, dusting or broadcasting agents or granules by spraying, atomizing, dusting, broadcasting or watering. The application forms depend on the purpose for which they are used; they ought in every case to ensure the finest possible distribution of the active ingredients according to the invention.

Suitable for preparing directly sprayable solutions, emulsions, pastes or oil dispersions are mineral oil fractions of moderate to high boiling point such as kerosene or diesel oil, also coaltar oils and oils of vegetable or animal origin, aliphatic, cyclic and aromatic hydrocarbons, e.g. benzene, toluene, xylene, paraffin, tetrahydronaphthalene, alkylated naphthalenes or derivatives thereof, methanol, ethanol, propanol, butanol, chloroform, tetrachloromethane, cyclohexanol, cyclohexanone, chlorobenzene, isophorone or highly polar solvents such as dimethylformamide, dimethyl sulfoxide, N-methylpyrrolidone or water.

Aqueous application forms can be prepared from emulsion concentrates, pastes or wettable powders (oil dispersions) by adding water. To prepare emulsions, pastes or oil dispersions, the substances can be homogenized, as such or dissolved in an oil or solvent, using wetting agents, adhesion promoters, dispersants or emulsifiers, in water. However, it is also possible to prepare concentrates which are composed of active substance, wetting agent, adhesion promoter, dispersant or emulsifier and, where appropriate, solvent or oil and which are suitable for dilution with water.

Suitable surfactants are the alkali metal, alkaline earth metal and ammonium salts of lignin-, phenol-, naphthalene- and dibutylnaphthalenesulfonic acid, alkyl- and alkylarylsulfonates, alkyl sulfates, fatty alcohol sulfates and fatty acids, and the alkali metal and alkaline earth metal salts thereof, salts of sulfated fatty alcohol glycol ether, products of the condensation of sulfonated naphthalene and naphthalene derivatives with formaldehyde, products of the condensation of naphthalene or naphthalenesulfonic acid with phenol and formaldehyde, polyoxyethylene octylphenol ether, ethoxylated isooctyl-, octyl- or nonylphenol, alkylphenol and tributylphenyl polyglycol ethers, alkylaryl polyether alcohols, isotridecyl alcohol, fatty alcohol/ethylene oxide condensates, ethoxylated castor oil, polyoxyethylene alkyl ethers, ethoxylated polyoxypropylene, lauryl alcohol polyglycol ether acetal, sorbitol esters, ligninsulfite waste liquors and methylcellulose.

Powders and dusting and broadcasting agents can be prepared by mixing or grinding the active substances together with a solid carrier.

The formulations generally contain from 0.01 to 95% by weight, preferably from 0.1 to 90% by weight, of active ingredient. The active ingredients are employed in a purity of from 90 to 100%, preferably 95 to 100% (according to the NMR spectrum).

Examples of formulations are:

I. an intimate mixture of 5 parts by weight of compound No. 1.01 and 95 parts by weight of finely divided kaolin; this dusting agent contains 5% by weight of active ingredient;

II. an intimate mixture of 30 parts by weight of compound No. 2.01, 92 parts by weight of powdered silica gel and 8 parts by weight of liquid paraffin which was sprayed onto the surface of this silica gel; this formulation confers good adhesion on the active ingredient (content of active ingredient 23% by weight);

III. a solution of 10 parts by weight of compound No. 3.01, 90 parts by weight of xylene, 6 parts by weight of the adduct of 8 to 10 moles of ethylene oxide and 1 mole of oleic acid N-monoethanolamide, 2 parts by weight of calcium dodecylbenzenesulfonate and 2 parts by weight of the adduct of 40 moles of ethylene oxide and 1 mole of castor oil (content of active ingredient 9% by weight);

IV. a solution of 20 parts by weight of compound No. 4.01, 60 parts by weight of cyclohexanone, 30 parts by weight of isobutanol, 5 parts by weight of the adduct of 7 moles of ethylene oxide and 1 mole of isooctylphenol and 5 parts by weight of the adduct of 40 moles of ethylene oxide and 1 mole of castor oil (content of active ingredient 16% by weight);

V. a mixture, ground in a hammer mill, of 80 parts by weight of compound No. 5.01, 3 parts by weight of sodium diisobutylnaphthalene-α-sulfonate, 10 parts by weight of the sodium salt of a ligninsulfonic acid from a sulfite waste liquor and 7 parts by weight of powdered silica gel (content of active ingredient 80% by weight); a fine dispersion of this mixture in water can be used for spraying;

VI. a solution of 90 parts by weight of compound No. 6.01 and 10 parts by weight of N-methyl-α-pyrrolidone is suitable for use in the form of very small drops (content of active ingredient 90% by weight);

VII. a solution of 20 parts by weight of compound No. 2.02, 40 parts by weight of cyclohexanone, 30 parts by weight of isobutanol, 20 parts by weight of the adduct of 7 moles of ethylene oxide and 1 mole of isooctylphenol and 10 parts by weight of the adduct of 40 moles of ethylene oxide and 1 mole of castor oil; a fine dispersion of this solution in 100,000 parts by weight of water contains 0.02% by weight of the active ingredient;

VIII. a mixture, ground in a hammer mill, of 20 parts by weight of compound No. 3.02, 3 parts by weight of sodium diisobutylnaphthalene-α-sulfonate, 17 parts by weight of the sodium salt of a ligninsulfonic acid from a sulfite waste liquor and 60 parts by weight of powdered silica gel; a fine dispersion of the mixture in 20,000 parts by weight of water contains 0.1% by weight of active ingredient and can be used for spraying.

Granules, e.g. coated, impregnated or homogeneous granules, can be prepared by binding the active ingredients to solid carriers. Examples of solid carriers are mineral earths such as silica gel, silicic acids, silicates, talc, kaolin, attapulgite, limestone, lime, chalk, bole, loess, clay, dolomite, diatomaceous earth, calcium and magnesium sulfates, magnesium oxide, ground plastics, fertilizers such as ammonium sulfate, ammonium phosphate, ammonium nitrate, ureas and vegetable products such as cereals flour, bark meal, wood meal and nutshell meal, cellulose powders or other solid carriers.

The agents generally contain from 0.1 to 95% by weight of active ingredient, preferably from 0.5 to 90% by weight.

The concentrations of active ingredients in the formulations ready for use can vary within wide limits. They are generally from 0.0001 to 10%, preferably from 0.01 to 1%.

The active ingredients can also be used successfully in the ultra low volume (ULV) method, in which case it is possible to apply formulations containing more than 95% by weight of active ingredient or even the pure active ingredient.

The application rate of active ingredient in the open is from 0.02 to 10, preferably 0.1 to 2.0, kg/ha.

The active ingredients can be mixed with oils of various types, herbicides, fungicides, other pesticides, bactericides, where appropriate just before use (tank mix). These agents can be mixed with the novel agents in the ratio of from 1:10 to 10:1 by weight.

PREPARATION EXAMPLES

N-[4-(2,4-Dichlorophenyl)-2-thiazolyl]-2,4-dinitro-6-trifluoromethylaniline

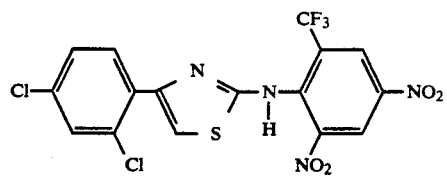

A solution of 7.4 g (66 mmol) of potassium tert-butylate in 50 ml of tert-butanol was added dropwise to a vigorously stirred mixture of 8.0 g (33 mmol) of 2-amino-4-(2,4-dichlorophenyl)thiazole, 9.8 g (37 mmol) of 2,4-dinitro-6-trifluoromethylchlorobenzene and 100 ml of tetrahydrofuran/tert-butanol (1:2) at 0° to 5° C. in such a way that addition was complete after 1 hour. After a further hour at 0° C., the mixture was slowly warmed, over the course of about 2 hours, to 20° C. The mixture was then adjusted to pH 4 with glacial acetic acid and diluted with about 1 l of water. The precipitate was separated off, washed with water until neutral and dried. Yield: 90%; melting point 125° to 130° C.

Further compounds Ia which were or can be prepared in the same way are listed in the table which follows.

TABLE

Ia $$\text{Het—N}(Q)\text{—}\langle\text{aryl}\rangle\text{-R}^2,\text{R}^3,\text{NO}_2,\text{R}^1$$

| No. | Het | Q | $R^1$ | $R^2$ | $R^3$ | m.p. [°C.] |
|---|---|---|---|---|---|---|
| 1.01 | 3-CN-4-$CH_3$-5-$COOCH_3$-thien-2-yl | H | Cl | $CF_3$ | $NO_2$ | 189–190 |
| 1.02 | 3-CN-4-$CH_3$-5-$COOCH_3$-thien-2-yl | H | H | $CF_3$ | $NO_2$ | 202–204 |
| 1.03 | 3-CN-4-$CH_3$-5-$COOCH_3$-thien-2-yl | H | H | $NO_2$ | $CF_3$ | 164–165 |
| 1.04 | 4-$CH_3$-3,5-$(COOC_2H_5)_2$-thien-2-yl | H | Cl | $CF_3$ | $NO_2$ | 121–123 |
| 1.05 | 4-$CH_3$-3,5-$(COOC_2H_5)_2$-thien-2-yl | H | H | $CF_3$ | $NO_2$ | 178–179 |
| 1.06 | 4-$CH_3$-3,5-$(COOC_2H_5)_2$-thien-2-yl | H | H | $NO_2$ | $CF_3$ | 151–152 |
| 1.07 | 3-$COOC_2H_5$-4,5-$(CH_2)_4$-thien-2-yl | H | Cl | $CF_3$ | $NO_2$ | 115–116 |
| 1.08 | 3-$COOC_2H_5$-4,5-$(CH_2)_4$-thien-2-yl | H | H | $CF_3$ | $NO_2$ | 131–134 |
| 1.09 | 3-$COOC_2H_5$-4,5-$(CH_2)_4$-thien-2-yl | H | H | $NO_2$ | $CF_3$ | 152–153 |
| 1.10 | 3-CN-4-Cl-thien-2-yl | H | H | $NO_2$ | $CF_3$ | oil |
| 2.01 | 4-$COOCH_3$-thien-3-yl | H | H | $CF_3$ | $NO_2$ | 208–209 |
| 2.02 | 2-$COOCH_3$-4-$NO_2$-thien-3-yl | H | Cl | $CF_3$ | $NO_2$ | 170–171 |
| 2.03 | 2-$COOCH_3$-4-$NO_2$-thien-3-yl | H | H | $CF_3$ | $NO_2$ | 184–185 |
| 2.04 | 2-$COOCH_3$-4-$NO_2$-thien-3-yl | H | H | $NO_2$ | $CF_3$ | 141–143 |
| 2.05 | 2-$COOCH_3$-4-CN-5-$CH_3$-thien-3-yl | H | Cl | $CF_3$ | $NO_2$ | 122–125 |
| 2.06 | 2-$COOCH_3$-4-CN-5-$CH_3$-thien-3-yl | H | H | $CF_3$ | $NO_2$ | 166–168 |
| 2.07 | 2-$COOCH_3$-4-CN-5-$CH_3$-thien-3-yl | H | H | $NO_2$ | $CF_3$ | 130–134 |
| 3.01 | 3-$CH_3$-isothiazol-5-yl | H | Cl | $CF_3$ | $NO_2$ | 90–93 |
| 3.02 | 3-$CH_3$-isothiazol-5-yl | H | H | $CF_3$ | $NO_2$ | 111–114 |
| 3.03 | 3-$CH_3$-isothiazol-5-yl | H | H | $NO_2$ | $CF_3$ | 111–116 |
| 3.04 | 3-$CH_3$-4-SCN-isothiazol-5-yl | H | Cl | $CF_3$ | $NO_2$ | 126–128 |
| 3.05 | 3-$CH_3$-4-SCN-isothiazol-5-yl | H | H | $CF_3$ | $NO_2$ | 176–177 |
| 3.06 | 3-$CH_3$-4-Br-isothiazol-5-yl | H | Cl | $CF_3$ | $NO_2$ | 157–158 |
| 3.07 | 3-$CH_3$-4-Br-isothiazol-5-yl | H | H | $CF_3$ | $NO_2$ | 174–175 |
| 3.08 | 3-$CH_3$-4-Br-isothiazol-5-yl | H | H | $NO_2$ | $CF_3$ | 90–92 |
| 3.09 | 3-$C_6H_5$-4-CN-isothiazol-5-yl | H | Cl | $CF_3$ | $NO_2$ | 134–136 |
| 3.10 | 3-$C_6H_5$-4-CN-isothiazol-5-yl | H | H | $CF_3$ | $NO_2$ | 144–147 |
| 3.11 | 3-$C_6H_5$-4-CN-isothiazol-5-yl | H | H | $NO_2$ | $CF_3$ | 193–196 |
| 3.12 | 3-$CH_2C_6H_5$-4-CN-isothiazol-5-yl | H | Cl | $CF_3$ | $NO_2$ | 149–152 |
| 3.13 | 3-$CH_2C_6H_5$-4-CN-isothiazol-5-yl | H | H | $CF_3$ | $NO_2$ | 178–180 |
| 3.14 | 3-$CH_2C_6H_5$-4-CN-isothiazol-5-yl | H | H | $NO_2$ | $CF_3$ | 135–138 |
| 4.01 | Thiazol-2-yl | H | H | $NO_2$ | $CF_3$ | 197–200 |
| 4.02 | 5-Cl-thiazol-2-yl | H | Cl | $CF_3$ | $NO_2$ | 152–162 |
| 4.03 | 5-Cl-thiazol-2-yl | H | H | $CF_3$ | $NO_2$ | 132–134 |

TABLE-continued

Ia

Het—N(Q)—[phenyl with R³ at 5, R² at 4, R¹ at 3, NO₂ at 2]

| No. | Het | Q | R¹ | R² | R³ | m.p. [°C] |
|---|---|---|---|---|---|---|
| 4.04 | 5-Cl-thiazol-2-yl | H | H | $NO_2$ | $CF_3$ | 125–130 |
| 4.05 | 5-Br-thiazol-2-yl | H | Cl | $CF_3$ | $NO_2$ | 141–144 |
| 4.06 | 5-Br-thiazol-2-yl | H | H | $CF_3$ | $NO_2$ | 142–145 |
| 4.07 | 5-Br-thiazol-2-yl | H | H | CN | $NO_2$ | 156–158 |
| 4.08 | 5-Br-thiazol-2-yl | H | H | $NO_2$ | $CF_3$ | 64–67 |
| 4.09 | 5-$CH_3$-thiazol-2-yl | H | Cl | $CF_3$ | $NO_2$ | >220 |
| 4.10 | 5-$CH_3$-thiazol-2-yl | H | H | $CF_3$ | $NO_2$ | 122–130 |
| 4.11 | 5-$CH_3$-thiazol-2-yl | H | H | $NO_2$ | $CF_3$ | 168–171 |
| 4.12 | 5-$SCH_3$-thiazol-2-yl | H | Cl | $CF_3$ | $NO_2$ | 145–148 |
| 4.13 | 5-$SCH_3$-thiazol-2-yl | H | H | $CF_3$ | $NO_2$ | 122 |
| 4.14 | 5-$SCH_3$-thiazol-2-yl | H | H | $NO_2$ | $CF_3$ | 143–144 |
| 4.15 | 5-$COOCH_3$-thiazol-2-yl | H | Cl | $CF_3$ | $NO_2$ | 85–91 |
| 4.16 | 5-$COOCH_3$-thiazol-2-yl | H | H | $CF_3$ | $NO_2$ | 145–149 |
| 4.17 | 5-$COOCH_3$-thiazol-2-yl | H | H | $NO_2$ | $CF_3$ | 160–162 |
| 4.18 | 4-$COOC_2H_5$-thiazol-2-yl | H | Cl | $CF_3$ | $NO_2$ | 150 |
| 4.19 | 4-$COOC_2H_5$-thiazol-2-yl | H | H | $CF_3$ | $NO_2$ | 126–129 |
| 4.20 | 4-$COOC_2H_5$-thiazol-2-yl | H | H | $NO_2$ | $CF_3$ | 123–124 |
| 4.21 | 4-Adamantyl-thiazol-2-yl | H | Cl | $CF_3$ | $NO_2$ | 197–198 |
| 4.22 | 4-Adamantyl-thiazol-2-yl | H | H | $CF_3$ | $NO_2$ | 147–148 |
| 4.23 | 4-Adamantyl-thiazol-2-yl | H | H | $NO_2$ | $CF_3$ | 133–134 |
| 4.24 | 4-(2,4-$Cl_2$—$C_6H_3$)-thiazol-2-yl | H | Cl | $CF_3$ | $NO_2$ | 203–208 |
| 4.25 | 4-(2,4-$Cl_2$—$C_6H_3$)-thiazol-2-yl | H | H | $CF_3$ | $NO_2$ | 148–157 |
| 4.26 | 4-(2,4-$Cl_2$—$C_6H_3$)-thiazol-2-yl | H | H | $NO_2$ | $CF_3$ | 191–194 |
| 4.27 | 4-(4-F—$C_6H_4$)-thiazol-2-yl | H | Cl | $CF_3$ | $NO_2$ | 175–176 |
| 4.28 | 4-(4-F—$C_6H_4$)-thiazol-2-yl | H | H | $CF_3$ | $NO_2$ | 177–179 |
| 4.29 | 4-(4-F—$C_6H_4$)-thiazol-2-yl | H | H | $NO_2$ | $CF_3$ | 158–160 |
| 4.30 | 4-(4-Cl-Naphth-1-yl)-thiazol-2-yl | H | Cl | $CF_3$ | $NO_2$ | >220 |
| 4.31 | 4-(4-Cl-Naphth-1-yl)-thiazol-2-yl | H | H | $NO_2$ | $CF_3$ | >220 |
| 4.32 | 4-(5-Cl-Thien-2-yl)-thiazol-2-yl | H | H | $CF_3$ | $NO_2$ | 176–178 |
| 4.33 | 4-(Thien-2-yl)-thiazol-2-yl | H | Cl | $CF_3$ | $NO_2$ | 148–151 |
| 4.34 | 4-Cl-5-$CF_3$-thiazol-2-yl | H | Cl | $CF_3$ | $NO_2$ | oil |
| 4.35 | 4-CN-5-N(allyl)$_2$-thiazol-2-yl | H | Cl | $CF_3$ | $NO_2$ | 125–130 |
| 5.01 | 5-Br-(1,3,4-thiadiazol-2-yl) | H | Cl | $CF_3$ | $NO_2$ | 211–213 |
| 5.02 | 5-Br-(1,3,4-thiadiazol-2-yl) | H | H | $CF_3$ | $NO_2$ | 217–218 |
| 5.03 | 5-Br-(1,3,4-thiadiazol-2-yl) | H | H | $NO_2$ | $CF_3$ | 168–169 |
| 5.04 | 5-$CH_3$-(1,3,4-thiadiazol-2-yl) | H | Cl | $CF_3$ | $NO_2$ | 131–134 |
| 5.05 | 5-$CH_3$-(1,3,4-thiadiazol-2-yl) | H | $OCH_3$ | $CF_3$ | $NO_2$ | 128–132 |
| 5.06 | 5-$CH_3$-(1,3,4-thiadiazol-2-yl) | H | H | $NO_2$ | Cl | 195–197 |
| 5.07 | 5-$CH_3$-(1,3,4-thiadiazol-2-yl) | H | H | $NO_2$ | $CF_3$ | 162–164 |
| 5.08 | 5-(4-Cl—$C_6H_4$)-(1,3,4-thiadiazol-2-yl) | H | Cl | $CF_3$ | $NO_2$ | 193–196 |
| 5.09 | 5-(4-Cl—$C_6H_4$)-(1,3,4-thiadiazol-2-yl) | H | H | $CF_3$ | $NO_2$ | 210–214 |
| 5.10 | 5-(4-Cl—$C_6H_4$)-(1,3,4-thiadiazol-2-yl) | H | H | $NO_2$ | $CF_3$ | 151–154 |
| 5.11 | 5-$CF_3$-(1,3,4-thiadiazol-2-yl) | H | Cl | $CF_3$ | $NO_2$ | 177–181 |
| 5.12 | 5-$CF_3$-(1,3,4-thiadiazol-2-yl) | H | H | $CF_3$ | $NO_2$ | 195–196 |
| 5.13 | 5-$CF_3$-(1,3,4-thiadiazol-2-yl) | H | H | $NO_2$ | $CF_3$ | 176–183 |
| 5.14 | 5-$CF_3$-(1,3,4-thiadiazol-2-yl) | H | $OCH_3$ | $CF_3$ | $NO_2$ | 158–160 |
| 5.15 | 5-$CF_3$-(1,3,4-thiadiazol-2-yl) | H | H | CN | $NO_2$ | >220 |
| 5.16 | 5-$CF_3$-(1,3,4-thiadiazol-2-yl) | H | H | $NO_2$ | Cl | 191–193 |
| 5.17 | 5-$CF_3$-(1,3,4-thiadiazol-2-yl) | H | H | $NO_2$ | $CHCH_3C_2H_5$ | 192–194 |
| 6.01 | 3-$SCH_3$-(1,2,4-thiadiazol-5-yl) | H | Cl | $CF_3$ | $NO_2$ | 112–116 |
| 6.02 | 3-$SCH_3$-(1,2,4-thiadiazol-5-yl) | H | H | $CF_3$ | $NO_2$ | 146–148 |
| 6.03 | 3-$SCH_3$-(1,2,4-thiadiazol-5-yl) | H | H | $NO_2$ | $CF_3$ | resin |
| 7.01 | 5-Cl-thiazol-2-yl | $N(n-C_4H_9)_4$ | Cl | $CF_3$ | $NO_2$ | 64–66 |
| 7.02 | 4-(2,4-$Cl_2$—$C_6H_3$)thiazol-2-yl | $N(n-C_4H_9)_4$ | H | $NO_2$ | $CF_3$ | 90–96 |

EXAMPLES of USE

The insecticidal action of the compounds of the formulae Ia and Ib was demonstrated in the following tests:
The active ingredients were prepared
a) as 0.1% strength solution in acetone or
b) as 10% strength emulsion in a mixture of 70% by weight cyclohexanol, 20% by weight Nekanil ® LN (Lutensol ® AP6, wetting agent with emulsifying and dispersing action based on ethoxylated alkylphenols) and 10% by weight Emulphore ® EL (Emulane ® EL, emulsifier based on ethoxylated fatty alcohols) and diluted to the required concentration with acetone in the case of a) or with water in the case of b).

After completion of the tests, in each case the lowest concentration at which the compounds still caused 80–100% inhibition or mortality compared with untreated control tests (action threshold or minimal concentration) was determined.

Test A

*Caenorhabditis elegans* (free-living nematodes), contact action

The soil of a test vessel was wetted with an acetone solution of the active ingredient and, after the solvent had evaporated off, covered with 30 μl of *E. coli* bacteria suspension as nutrient medium and infected with 50 μl of nematode suspension.

The mortality rate was determined after 48 h.

In this test, compounds 1.1, 1.6, 1.9, 2.4, 2.7, 3.1, 3.3, 4.2, 4.5, 4.12, 4.14, 4.17, 4.27, 4.29, 4.31, 4.32, 4.34, 5.1, 5.3, 5.8, 5.10, 5.12, 6.1, 6.2 and 6.3 had action thresholds of from 0.4 to 100 ppm.

Test B

*Tetranychus telarius* (red spider mite), contact action

Potted bush beans which had formed the second pair of leaves and were heavily infested with spider mites were sprayed to run off with aqueous formulations containing various concentrations of active ingredient. This entailed the plants being sprayed on a rotating plate from all sides with about 50 ml of the spray liquor.

After 5 days in a glasshouse, the success of control was determined under a microscope (binocular).

In this test, compounds 3.3, 3.8, 4.14, 4.17, 4.26 and 5.7 had action thresholds of from 200 to 1000 ppm.

Test C

*Plutella maculipennis* (cabbage moth caterpillar), contact action

Leaves of young cabbage plants were wetted with the aqueous formulation of active ingredient and then placed on a moistened filter. 10 caterpillars in the 4th stage of development were then placed on each of the prepared leaves.

The mortality rate was determined after 48 h.

In this test, compounds 3.3, 3.7, 3.8, 4.11, 4.25, 4.26, 4.29, 4.32, 5.3, 5.7, 5.10, 5.15, 5.17, 6.2 and 6.3 had action thresholds of from 40 to 1000 ppm.

We claim:

1. An N-hetaryl-2-nitroaniline of the formula Ia or Ib

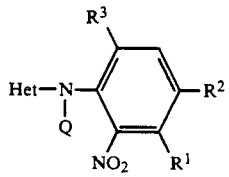

Ia

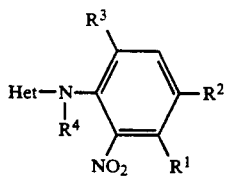

Ib where $R^1$ is hydrogen, halogen or $C_1$-$C_4$-alkoxy;

$R^2$ is nitro, cyano, halogen, partially or completely halogenated $C_1$-$C_4$-alkyl;

$R^3$ is nitro, halogen, $C_1$-$C_6$-alkyl, partially or completely halogenated $C_1$-$C_4$-alkyl;

$R^4$ is —CO—$R^5$, —CO—$OR^5$ or —$SO_2R_5$, with $R^5$ being $C_1$-$C_4$-alkyl, phenyl or naphthyl, both of which can carry up to 3 halogen atoms and/or $C_1$-$C_4$-alkyl groups;

Q is hydrogen, an alkali metal or alkaline earth metal ion, an ammonium ion whose nitrogen can carry up to four $C_1$-$C_4$ -alkyl, hydroxy-$C_1$-$C_4$-alkyl, phenyl and/or benzyl substituents, a phosphonium, sulfonium or sulfoxonium ion or an equivalent of a transition metal cation;

Het is thienyl, isothiazolyl or thiadiazolyl, each of which is linked via a ring carbon to the basic structure to which a non-aromatic $C_5$-$C_8$-ring can be fused and which can additionally carry on each other carbon one of the following substituents: cyano, thiocyanato, nitro, halogen, $C_1$-$C_4$-alkyl, partially or completely halogenated $C_1$-$C_4$-alkyl, $C_3$-$C_{10}$-cycloalkyl, $C_1$ -$C_4$-alkoxy, $C_1$-$C_4$-alkylthio, phenyl, naphthyl, benzyl or thienyl, where each aromatic ring can carry up to three halogen atoms and/or $C_1$-$C_4$-alkyl groups; CO—$R^5$, CO—$OR^5$, $NR^6R^7$, where $R^6$ and $R^7$ are $C_1$-$C_4$-alkyl, $C_2$-$C_4$-alkenyl, $C_2$-$C_4$-alkynyl, or the substituents on the two adjacent carbon atoms form a $C_3$-$C_6$-methylene chain excepting those compounds of Ia where simultaneously $R^1$ is hydrogen, $R^2$ and/or $R^3$ is nitro and Het is 1,3,4-thiadiazol-2-yl which is substituted by trifluoromethyl or tert-butyl.

2. An N-hetaryl-2-nitroaniline of the formula Ia as claimed in claim 1.

3. A method for controlling insects, arachnids or nematode which comprises exposing these pests and/or their habitat to an N-hetaryl-2-nitroaniline of the formula Ia and/or Ib

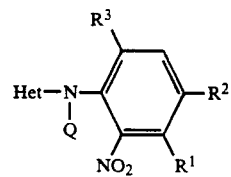

Ia

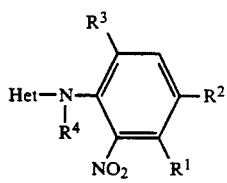

Ib where $R^1$ is hydrogen, halogen or $C_1$-$C_4$-alkoxy;

$R^2$ is nitro, cyano, halogen, partially or completely halogenated $C_1$-$C_4$-alkyl;

$R^3$ is nitro, halogen, $C_1$-$C_6$-alkyl, partially or completely halogenated $C_1$-$C_4$-alkyl;

$R^4$ is —CO—$R^5$, —CO—$OR^5$ or —$SO_2R_5$, with $R^5$ being $C_1$-$C_4$-alkyl, phenyl or naphthyl, both of which can carry up to 3 halogen atoms and/or $C_1$-$C_4$-alkyl groups;

Q is hydrogen, an alkali metal or alkaline earth metal ion, an ammonium ion whose nitrogen can carry up to four $C_1$-$C_4$ -alkyl, hydroxy-$C_1$-$C_4$-alkyl, phenyl and/or benzyl substituents, a phosphonium, sulfonium or sulfoxonium ion or an equivalent of a transition metal cation;

Het is thienyl, thiazolyl, isothiazolyl or thiadiazolyl, each of which is linked via a ring carbon to the basic element to which a non-aromatic $C_5$-$C_8$-ring can be fused and/or which can additionally carry on each other carbon one of the following substituents: cyano, thiocyanato, nitro, halogen, $C_1$-$C_4$-alkyl, partially or completely halogenated $C_1$-$C_4$-alkyl, $C_3$-$C_{10}$-cycloalkyl, $C_1$ -$C_4$-alkoxy, $C_1$-$C_4$-alkylthio, phenyl, naphthyl, benzyl or thienyl, where each aromatic ring can carry up to three halogen atoms and/or $C_1$-$C_4$-alkyl groups; CO—$R^5$, CO—$OR^5$, $NR^6R^7$, where $R^6$ and $R^7$ are $C_1$-$C_4$-alkyl, $C_2$-$C_4$-alkenyl or $C_2$-$C_4$-alkynyl.

4. The method of claim 3, wherein the insects, arachnids or nematodes and/or their habitat are exposed to an N-hetaryl-2-2-nitroaniline of the formula Ia in an amount sufficient for pesticidal activity.

* * * * *